(12) United States Patent
Chen et al.

(10) Patent No.: US 8,426,810 B2
(45) Date of Patent: Apr. 23, 2013

(54) METHOD OF PLANAR IMAGING ON SEMICONDUCTOR CHIPS USING FOCUSED ION BEAM

(75) Inventors: Bi-Jen Chen, Taoyuan County (TW); Pei-Yi Chen, Taoyuan County (TW); Chiu Chu Liu, Hsinchu County (TW)

(73) Assignee: Inotera Memories, Inc., Taoyuan County (TW)

( * ) Notice: Subject to any disclaimer, the term of this patent is extended or adjusted under 35 U.S.C. 154(b) by 0 days.

(21) Appl. No.: 13/348,734

(22) Filed: Jan. 12, 2012

(65) Prior Publication Data

US 2013/0068948 A1  Mar. 21, 2013

(30) Foreign Application Priority Data

Sep. 16, 2011 (TW) .............................. 100133429 A

(51) Int. Cl.
*H01J 49/00* (2006.01)
*B01D 59/44* (2006.01)

(52) U.S. Cl.
USPC ........... 250/309; 250/306; 250/307; 250/310; 250/311; 250/398

(58) Field of Classification Search ............... 250/492.1, 250/492.2, 492.21, 492.3, 493.1, 398, 309, 250/306, 307, 311
See application file for complete search history.

(56) References Cited

U.S. PATENT DOCUMENTS

| | | | |
|---|---|---|---|
| 6,259,106 B1 * | 7/2001 | Boegli et al. | 250/492.22 |
| 6,335,534 B1 * | 1/2002 | Suguro et al. | 250/492.21 |
| 6,433,347 B1 * | 8/2002 | Suzuki | 250/492.22 |
| 6,448,556 B1 * | 9/2002 | Cowley et al. | 250/311 |
| 7,326,927 B2 * | 2/2008 | Frosien | 250/310 |
| 7,554,097 B2 * | 6/2009 | Ward et al. | 250/423 F |
| 7,615,765 B2 * | 11/2009 | Katagiri et al. | 250/492.3 |
| 7,786,454 B2 * | 8/2010 | Parker | 250/492.23 |
| 7,842,920 B2 * | 11/2010 | Lundquist | 250/306 |
| 8,304,750 B2 * | 11/2012 | Preikszas et al. | 250/492.22 |
| 2007/0210250 A1 * | 9/2007 | Ward et al. | 250/307 |
| 2008/0142711 A1 * | 6/2008 | Lundquist | 250/307 |
| 2010/0294930 A1 * | 11/2010 | Preikszas et al. | 250/307 |

* cited by examiner

*Primary Examiner* — David A Vanore
(74) *Attorney, Agent, or Firm* — Rosenberg, Klein & Lee

(57) ABSTRACT

A method of planar imaging on semiconductor chips using focused ion beam includes the initial step of disposing at least a positioning symbol to designate a testing area. A metal membrane is positioned on the testing area. The testing chip is trimmed to form a first testing chip. A blind opening is cut proximate to the testing area on the first testing chip forms a second testing chip. The second testing chip is mounted on an inclinable platform. The mounted second testing chip is rotated with the inclinable platform. Ion beams are emitted into the opening at an angle of inclination. Ion beams are emitted in the direction of the incident ray to form planar images of different depths parallel to the metal membrane on the testing area.

10 Claims, 6 Drawing Sheets

METHOD OF PLANAR IMAGING ON SEMICONDUCTOR CHIPS USING FOCUSED ION BEAM

BACKGROUND OF THE INVENTION

1. Field of the Invention

The present invention relates to a method of planar imaging on chips; in particular, to a method of planar imaging on semiconductor chips using Focused Ion Beam (FIB).

2. Description of Related Art

Due to the advance of technology, the development on manufacturing products tend to pursue microminiaturization; in terms of the semi-conductor industry, the micro structure of the semi-conductor chips is unable to be detected through naked eyes, therefore, auxiliary machineries are required to assist men in finding the defects as well as learning the actual structures of the micro chips.

The manufacture process of a chip wherein different semiconductor components are formed on the surface of the substrate to form a thin slice-like chip, the defect of the chips often was formed in the semi-conductor components, therefore to detect the defect features, a method of direct observation is implemented by taking a top view and extract images of the substrate position from the chip surface. The conventional method uses the Scanning Electro Microscope to form a horizontal image of the chip on the surface thereof, after the image is obtained, remove the surface layer by artificial polishing before beginning the second extraction of the image. In other words, by polishing the testing chip one time after another, the image of the testing surface is obtained gradually, so as to detect the position and the feature of the defects hidden within the chip. However, the major disadvantage of this method is that the defect features may be removed during polishing as the thickness of the layer removed through polishing is unable to get thinner, resulting the lost of opportunity in observing as well as a higher time consumption and failing rate.

As shown in FIG. 1, another conventional method of detecting defects uses the Focused Ion Beam, as ion beams in the direction of the incident ray B are perpendicularly emitted into the chip surface 2' of the chip 1, a vertical cross-sectional view perpendicular to the chip surface 2' is formed. However, simply using the vertical cross-sectional view which is perpendicular to the chip surface 2' is unable to detect the defect features of the chip 1 completely. Furthermore, the testing chip has to be cut into the minimized state before examine, and this usually results the testing chip to be too thin or small, therefore easily loss during testing, resulting additional grids required to place the chip within hence raising the total expense.

Thus, polishing the chip in the testing area to extract images of different depths through electron microscope, or obtain the vertical cross-sectional view of the chip perpendicular to the testing area by using Focused Ion Beam, either method have disadvantages such as high time, human resource and money consumption and high failing rate.

SUMMARY OF THE INVENTION

The object of the present invention is to provide a method of planar imaging on semiconductor chips using focused ion beam, comprising the steps of: (A)disposing at least a positioning symbol to designate a testing area thereon; (B)disposing a metal membrane on the testing area; (C)trimming the testing chip to form a first testing chip; (D)cutting a blind opening proximate the testing area on the first testing chip to form a second testing chip; (E)disposing and erecting the second testing chip on an inclinable platform; (F)rotating the erected second testing chip with the inclinable platform, thereby allowing ion beams from the FIB to emit into the opening in an angle of inclination; (G)emitting ion beams in the direction of the incident ray to form planar images of different depths parallel to the testing area of the metal membrane.

The present invention has the following advantages: the present invention utilizes the focused ion beam to perform planar imaging on the testing chips, this raises the chance of revealing micro defect features on the image; it is also capable of avoiding the condition when conventional method using electron microscope to extract planar images in the testing area, the test accuracy is restricted by the imprecisely controlled polishing depths, resulting the defect features to be removed during the polishing process hence increases the failing rate; and the disadvantages of polishing include requiring vast amount of human power and high time consumption and etc. On the other hand, conventionally, the vertical cross-sectional view, perpendicular to the chip surface, extracted by the focused ion beam has disadvantages such as incapability to reveal the defect features of the chips completely and etc. In comparison, the present invention provide another view to see the defect vertical outlook that easy to understand overall outlook if combine vertical and perpendicular SEM image and the testing chips are also larger in volume, this reduces the risk of losing the chips while testing and also increases the chances to succeed.

In order to further the understanding regarding the present invention, the following embodiments are provided along with illustrations to facilitate the disclosure of the present invention.

DETAILED DESCRIPTION OF THE PREFERRED EMBODIMENTS

The aforementioned illustrations and following detailed descriptions are exemplary for the purpose of further explaining the scope of the present invention. Other objectives and advantages related to the present invention will be illustrated in the subsequent descriptions and appended drawings.

Figure 1:
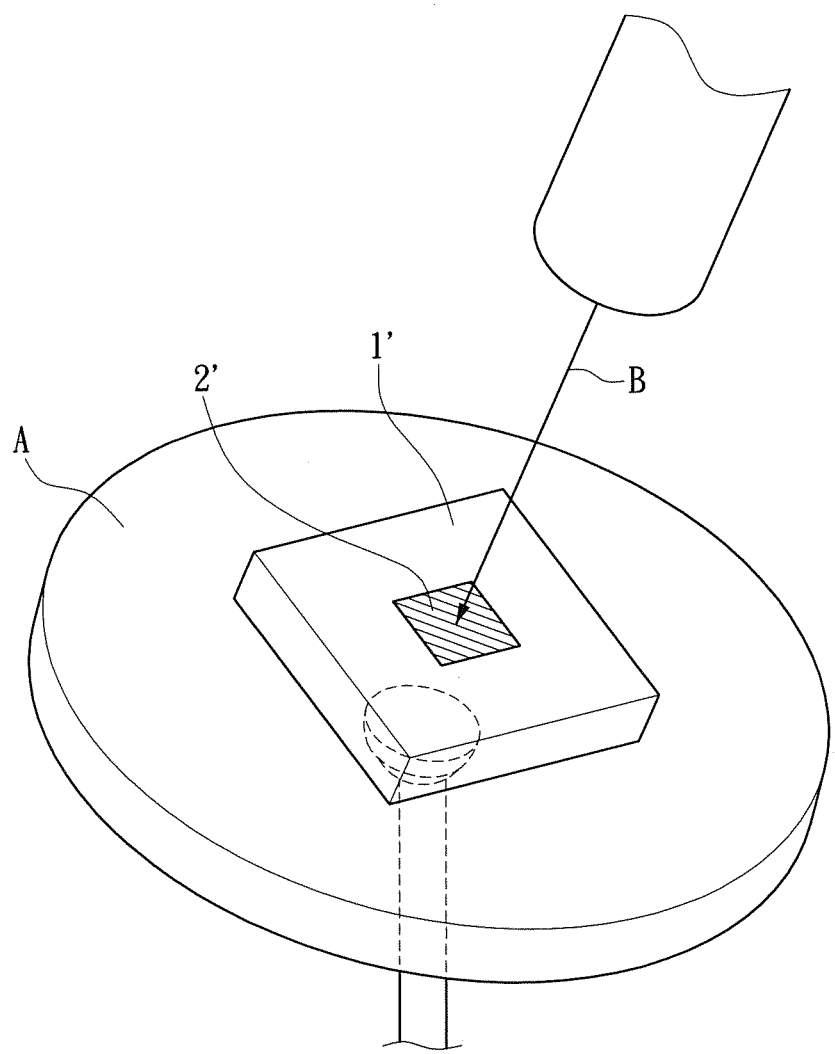
FIG. 1 shows a perspective view of a conventional method of planar imaging on chips by using focused ion beam.
Figure 2:
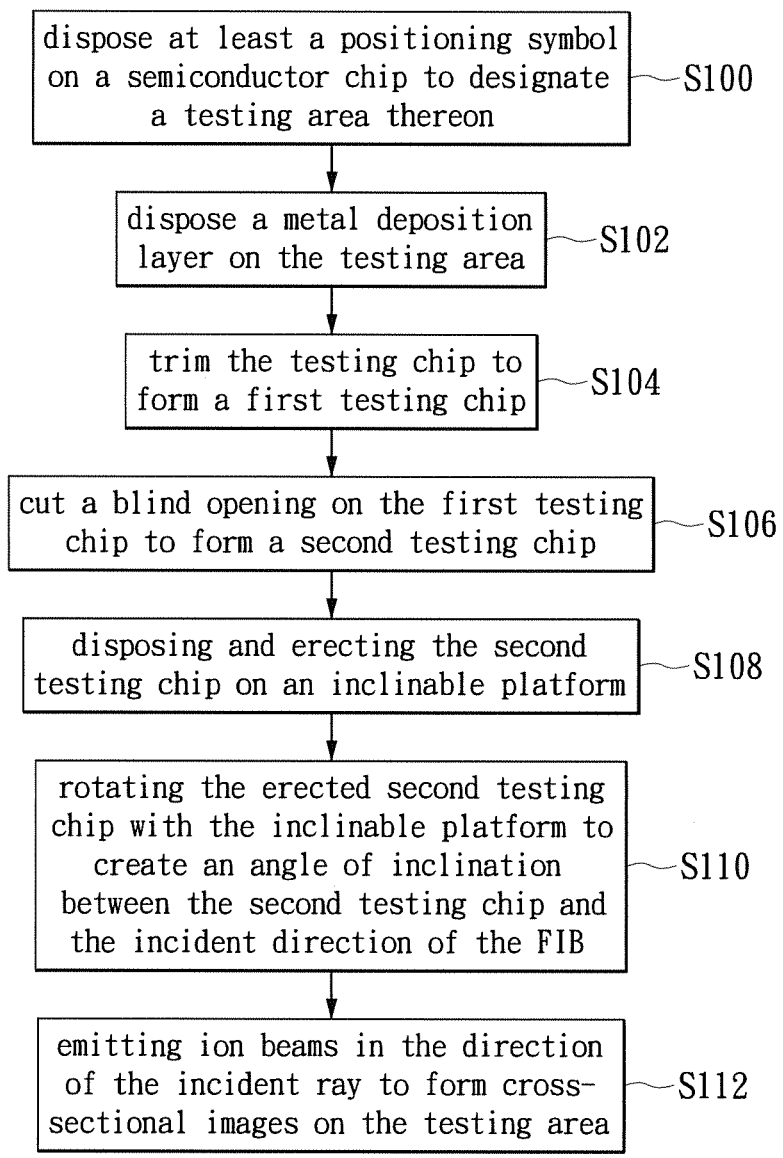
FIG. 2 shows a flow chart of a method of planar imaging on chips by using focused ion beam in accordance with the present invention.

FIG. 2 shows a flow chart of a method of planar imaging on chips by using FIB in accordance with the present invention.

Figure 3:
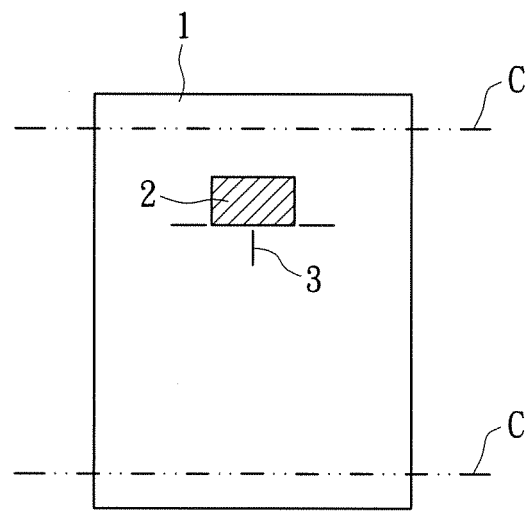
FIG. 3 shows a perspective planar view of the testing chip in accordance to the present invention.

To begin with step S100 shown in FIG. 3, provide a testing chip 1 which is a chip including semi-conductor components. At least one positioning symbol 3 is arranged on a surface of the testing chip 1 to designate a position in the testing area. The methods of designating the positioning symbol 3 include forming at least a notch abut the testing area by either means of laser, FIB or other methods, so as to distinguish a testing location on the testing chip 1 from the other spaces thereon.

Continue with Step S102, form a metal membrane 2 on the surface of the testing area wherein the methods of forming the metal layer 2 includes electroplating, vapor deposition, chemical deposition and etc. The instant embodiment utilizes the FIB to deposit the metal membrane 2, which is made of platinum or the chemical compounds thereof, on the surface of the testing area.

Figure 4:
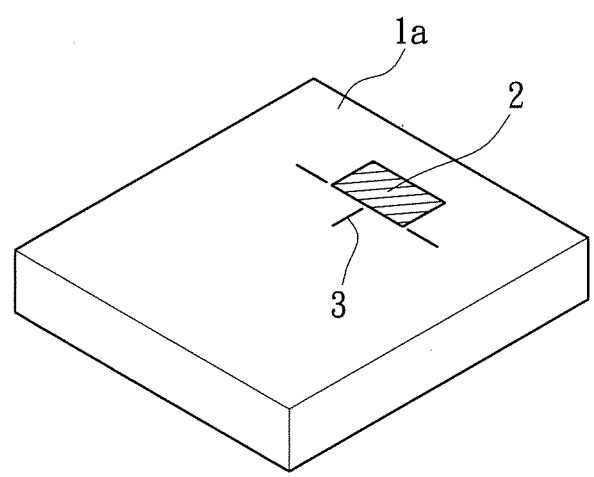
FIG. 4 shows a perspective view of the first testing chip in accordance to the present invention.

Referring now to FIGS. 3-4 for step S104. Trimming the testing chip 1 which includes the metal membrane 2 along the cutting lines C to form a first testing chip 1a wherein one of the cutting lines C should stay close to a border of the metal membrane 2. In particular, the width of the first testing chip 1a (the distance between the cutting lines C) is approximately 4 mm after cutting.

Figure 5:
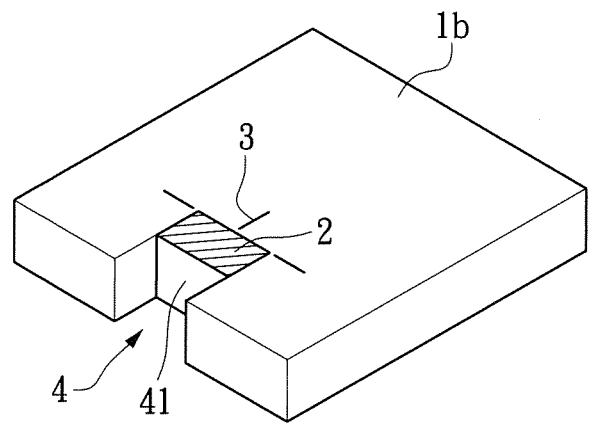
FIG. 5 shows a perspective view of the second testing chip in accordance to the present invention.

Please refer to FIGS. 4 and 5 for step S106. Realistically, due to the inaccuracy of dicing tool, there may be a distance remaining between the borders of the testing area and the first testing chip 1a. The positioning symbol 3 which adjoins the metal membrane 2 allows the FIB to find the location of the testing area quickly. The first testing chip 1a is then cut perpendicularly along a border of the metal membrane 2, forming an opening 4 on the first testing chip 1a wherein this structure is defined as a second testing chip 1B. Specifically, at least a positioning symbol 3 is arranged on a border of the metal membrane 2, away from the opening 4, to avoid the occurrence of Curtain Effect when cutting the positioning symbol 3, which may further influence the following procedures. The base surface of the opening 4 is a planar base 41 that adjoins the border of the metal membrane 2 and perpendiculars to the metal membrane 2.

Figure 6:
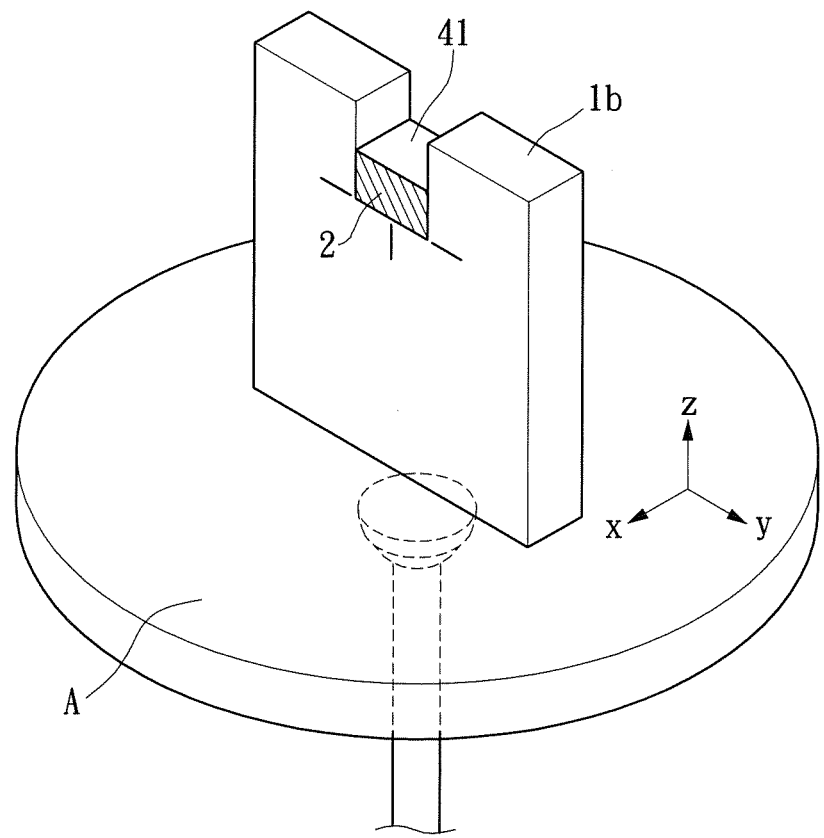
FIG. 6 shows a perspective view of the second testing chip deposited on the inclinable platform in accordance to the present invention.
Figure 7:
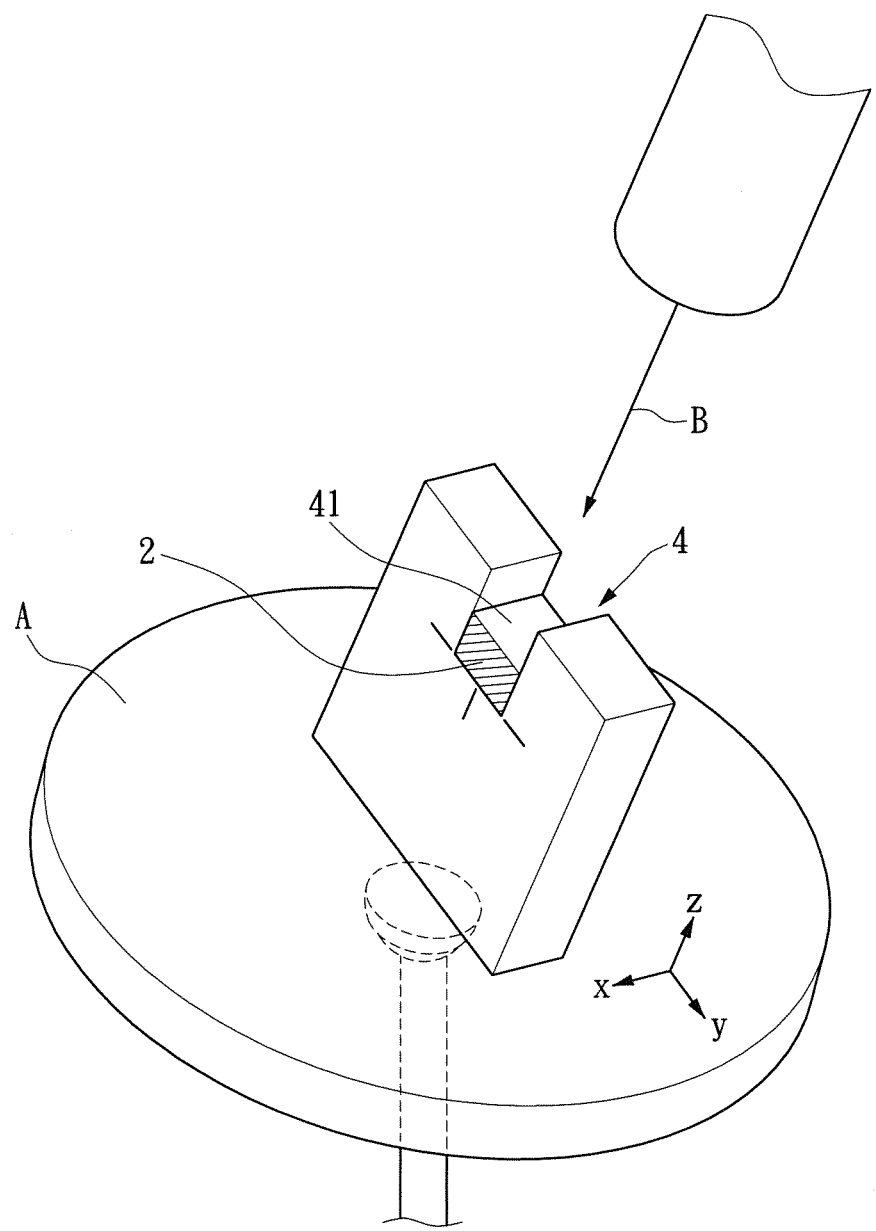
FIG. 7 shows a perspective view of the second testing chip deposited on the inclinable platform observing from the direction X in accordance to the present invention.

Referring now to FIGS. 6-7 for step S108. Erect the second testing chip 1b on the inclinable platform A with the opening 4 facing upwards and stabilized by means of clamping or gluing. To simplify the explanation of the relationship between the second testing chip 1b and the inclinable platform A, define a XYZ coordinate system on the second chip 1b wherein the X-axis refers to the normal vector of the metal membrane 2 and the Z-axis refers to the normal vector of the planar base 41 of the opening 4. To further explain, as the second testing chip 1b is stabilized on the inclinable platform A, the XYZ coordinate system varies as the inclinable platform A rotates, this also implies that the XYZ coordinate system is not an absolute coordinate system in the space.

Figure 8:
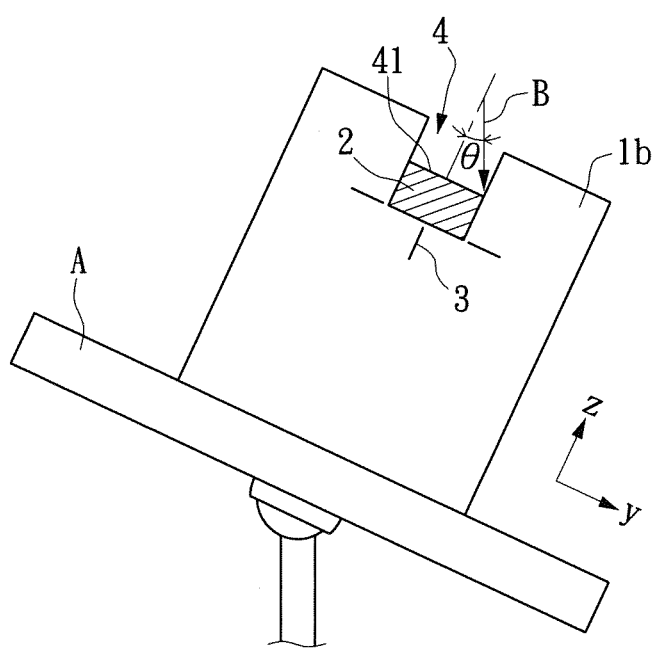
FIG. 8 shows a perspective view of the second testing chip and the incident direction of the FIB observing from the direction X in accordance to the present invention.

Refer to FIG. 7 for step S110. Begin with rotating the erected second testing chip 1b with the inclinable platform A to adjust the normal vector of the metal membrane 2 on the second testing chip 1b to an angle perpendicular to the incident direction B of the FIB. As the X-axis of the XYZ coordinate system is defined as the normal vector of the metal membrane 2, this implies that the incident direction B of the FIB is perpendicular to the X-axis; Referring now to FIGS. 7-8, as the X-axis of the XYZ coordinate system is perpendicular to the incident direction B of the FIB, by using the X-axis as the rotating axis to rotate the inclinable platform A, a non-zero included angle θ is formed between the normal vector of the planar base 41 of the second testing chip 1b on the inclinable platform A. In particular, as the Z-axis of the XYZ coordinate system is defined as the normal vector of the planar base 41 of the opening 4, this implies that the included angle θ formed between the incident direction B of the FIB and the Z-axis of the XYZ coordinate system is not zero. The included angle θ of the instant embodiment is not zero degree, to be specific, the included angle θ is 6-8 degree whereby the FIB emits ion beams into the opening 4 by using this angle of inclination.

Please refer to step S112 for FIG. 8. After the relative relationship between the second testing chip 1b and the FIB is established, the FIB emits ion beams into the testing area to form planar images of different depths and parallel to the metal membrane 2. This implies that several planar images are formed on the YZ planes under different values of X and thereby search the features and defects within the testing area.

A method of planar imaging on semiconductor chips using FIB of the present invention wherein the step S110, rotate the second testing chip to adjust the normal vector of the planar base of the opening (also referring to the Z-axis) to an angle unparallel to the incident direction of the FIB. This allows the ion beams to be emitted in an angle of inclination, thereby reducing the Curtain effect and also increases the number of times gaining cross-sectional views of different depths, so as to raise the chances of detecting defects features. Additionally, the testing chips cut in the present invention may include chips with larger volumes. The width of the testing chip in the instant embodiment is substantially 4 millimeters, but this is only an example and should not be limited to by this, also, comparing the testing chip with conventional testing chips (width approximately 20-40 micrometer), the testing chip of the instant embodiment are much larger in size, allowing picking up of the testing chips to be easier and reducing the possibilities of damaging and losing, and further achieve a higher possibility of extracting the images.

In conclusion, the present invention discloses a method of planar imaging on chips by using the FIB that can improve the condition of conventional methods, which often utilize scanning electron microscopes to obtain planar images from the testing area, whose test accuracy is restricted by the imprecisely controlled polishing depths through tradition abrasive processing. Also, the problem of being unable to obtain horizontal images when implementing the conventional method of using FIB to obtain images from testing area may be improved as well. The advantage of the present invention further includes cutting the test object into a larger volume by using the dicing tool and thereby prevents the condition of losing or damaging the testing chip while testing due to the micro size thereof, additionally, the larger volume of the testing chip can also exclude the utilization of grids which are used to place the testing chips within, hence increases cost-efficiency and chances of obtaining the images.

The descriptions illustrated supra set forth simply the preferred embodiments of the present invention; however, the characteristics of the present invention are by no means restricted thereto. All changes, alternations, or modifications conveniently considered by those skilled in the art are deemed to be encompassed within the scope of the present invention delineated by the following claims.

What is claimed is:

1. A method of planar imaging on semiconductor chips using focused ion beam (FIB), comprising the steps of:
    (A) disposing at least a positioning symbol on a semiconductor chip to designate a testing area thereon;
    (B) disposing a metal membrane on the testing area;
    (C) trimming the testing chip to form a first testing chip;
    (D) cutting a blind opening proximate the testing area on the first testing chip along a border of the metal membrane to form a second testing chip, wherein the base surface of the opening is substantially planar, wherein the at least one positioning symbol is positioned proximate a border of the metal membrane away from the opening;
(E) erecting the second testing chip on an inclinable platform with the opening facing upward;
(F) rotating the erected second testing chip with the inclinable platform so that the normal vector of the metal membrane is perpendicular to the incident direction of the FIB, wherein a non-zero included angle is formed between the normal vector of the base surface of the opening and the incident direction of the FIB, thereby allowing ion beams from the FIB to emit into the opening in an angle of inclination; and
(G) emitting ion beams in the direction of the incident ray to form planar images of different depths parallel to the metal membrane on the testing area.

2. The method of claim 1, wherein the method of designating a positioning symbol on the chip surface in step (A) includes using laser, FIB or other methods.

3. The method of claim 1, wherein the metal membrane is made of platinum or chemical compounds thereof.

4. The method of claim 1, wherein the step (C) includes using a dicing tool for trimming the chip.

5. The method according to claim 4, wherein the width of the first testing chip in step (C) is four millimeters.

6. The method of claim 1, wherein the step (D) includes using the FIB to cut the first testing chip to form the second testing chip.

7. The method according to claim 6, wherein the FIB in the step (D) utilizes at least one positioning symbol to locate a position about to be cut.

8. The method of claim 1, wherein the step (D) includes the base surface of the opening which adjoins the border of the metal membrane.

9. The method according to claim 8, wherein the step (E) includes stabilizing the second testing chip on the inclinable platform by means of clamping or gluing.

10. The method of claim 1, wherein the step (F) includes adjusting the angle of inclination to six to eight degree.

* * * * *